(12) United States Patent
Manavitehrani et al.

(10) Patent No.: US 12,246,111 B2
(45) Date of Patent: Mar. 11, 2025

(54) BIORESORBABLE IMPLANT WITH INSIDE-OUT RESORPTION FOR ENHANCED BONE INGROWTH AND TISSUE INTEGRATION AND METHOD OF MANUFACTURING THEREOF

(71) Applicant: SDIP Innovations Pty Ltd, San Francisco, CA (US)

(72) Inventors: Iman Manavitehrani, San Bruno, CA (US); Maryam Parviz, San Bruno, CA (US)

(73) Assignee: SDIP INNOVATIONS PTY LTD, Hornsby (AU)

( * ) Notice: Subject to any disclaimer, the term of this patent is extended or adjusted under 35 U.S.C. 154(b) by 135 days.

(21) Appl. No.: 17/163,113

(22) Filed: Jan. 29, 2021

(65) Prior Publication Data

US 2021/0236693 A1    Aug. 5, 2021

Related U.S. Application Data

(60) Provisional application No. 63/070,704, filed on Aug. 26, 2020, provisional application No. 62/968,056, filed on Jan. 30, 2020.

(51) Int. Cl.
| | |
|---|---|
| A61L 27/36 | (2006.01) |
| A61L 27/10 | (2006.01) |
| A61L 27/12 | (2006.01) |
| A61L 27/18 | (2006.01) |
| A61L 27/22 | (2006.01) |
| A61L 27/46 | (2006.01) |
| A61L 27/56 | (2006.01) |
| A61L 27/58 | (2006.01) |

(52) U.S. Cl.
CPC .......... *A61L 27/365* (2013.01); *A61L 27/10* (2013.01); *A61L 27/12* (2013.01); *A61L 27/18* (2013.01); *A61L 27/222* (2013.01); *A61L 27/3683* (2013.01); *A61L 27/46* (2013.01); *A61L 27/56* (2013.01); *A61L 27/58* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 3,921,636 A * | 11/1975 | Zaffaroni | A61F 6/14 424/431 |
| 6,599,516 B1 | 7/2003 | Knaack | |
| 2005/0251266 A1 | 11/2005 | Maspero et al. | |
| 2011/0106255 A1 | 5/2011 | Liu et al. | |
| 2011/0177134 A1 * | 7/2011 | Harmon | A61P 19/02 424/400 |
| 2012/0219635 A1 | 8/2012 | Liu | |
| 2014/0288663 A1 | 9/2014 | Borden et al. | |
| 2018/0168811 A1 | 6/2018 | Ranganathan et al. | |
| 2019/0083681 A1 * | 3/2019 | Bhumiratana | A61L 27/50 |

FOREIGN PATENT DOCUMENTS

| | | | | |
|---|---|---|---|---|
| CN | 102002142 A | 4/2011 | | |
| CN | 106267341 A | 1/2017 | | |
| CN | 109694494 A | 4/2019 | | |
| CN | 110563916 A | 12/2019 | | |
| CN | 110563917 A | 12/2019 | | |
| CN | 114085356 A | 2/2022 | | |
| JP | 2003335838 A | 11/2003 | | |
| WO | WO9109079 | * | 6/1991 | ........... A61K 9/1694 |
| WO | WO-9934772 A1 | * | 7/1999 | ............... A61K 8/19 |
| WO | WO-2015033939 A1 | 3/2015 | | |
| WO | 2019/232589 A1 | 12/2019 | | |
| WO | WO 2021/155248 A1 | 8/2021 | | |
| WO | WO 2024/062300 A1 | 3/2024 | | |

OTHER PUBLICATIONS

International Search Report, dated Apr. 23, 2021, for corresponding International Application No. PCT/US21/15852, 2 pages.
Written Opinion of the International Searching Authority, dated Apr. 23, 2021, for corresponding International Application No. PCT/US21/15852, 7 pages.
Zhong X. et al., "Fabrication of Biomimetic Poly(propylene carbonate) Scaffolds by Using Carbon Dioxide as a Solvent, Monomer and Foaming Agent", Green Chemistry, 2012, vol. 12, Issue 9, pp. 2523-2533, retrieved from the Internet: < DOI: 10.1039/C2GC35608B >.
Supplementary European Search report dated Jan. 4, 2024 in related European application No. 21747012.9 (eleven pages).
Manavitehrani Iman et al. "Formation of porous biodegradable scaffolds based on poly(propylene carbonate) using gas foaming technology", Materials Science and Engineering C, vol. 96, pp. 824-830, (Dec. 5, 2018).

(Continued)

*Primary Examiner* — David J Blanchard
*Assistant Examiner* — Daniel F Coughlin
(74) *Attorney, Agent, or Firm* — COOLEY LLP (57) ABSTRACT

Disclosed is a bioresorbable implant with enhanced bone ingrowth and tissue integration utilizing an inside-out resorption mechanism and a method to manufacture a bioresorbable implants for use in osteotomies and bone-soft tissue reconstruction surgeries. The bioresorbable implant includes a polymer A (e.g., an aliphatic polymer matrix) and/or poly(propylene fumarate)), a carbohydrate B (e.g., a bioresorbable natural carbohydrate filler) and a ceramic C. The implant may be a porous scaffold structures with suitable porosity, pore size, pore interconnectivity, and mechanical properties for enhanced osteoblast penetration and bone formation to fabricate tissue integrating bioresorbable implants. The implant may be shaped as wedges, bone void fillers, and soft tissue fixation implant like screws, rods and/or anchors. In some embodiments, the implant may be a putty.

8 Claims, 11 Drawing Sheets

(56) References Cited

OTHER PUBLICATIONS

Iman Manavitehrani et al., "Fabrication of a Biodegradable Implant with Tunable Characteristics for Bone Implant Applications", Biomacromolecules, vol. 18, No. 6, pp. 1736-1746 (May 23, 2017).
International Preliminary Report on Patentability dated Aug. 11, 2022 in related PCT/US2021/015852.
International Search Report and Written Opinion mailed Sep. 29, 2023 for International Application No. PCT/IB2023/058206, 10 pages.
Manavitehrani, I. et al., "Reinforced Poly(Propylene Carbonate) Composite with Enhanced and Tunable Characteristics, an Alternative for Poly(lactic Acid)," ACS Appl. Mater. Interfaces, 7:22421-22430 (2015).

\* cited by examiner

BIORESORBABLE IMPLANT WITH INSIDE-OUT RESORPTION FOR ENHANCED BONE INGROWTH AND TISSUE INTEGRATION AND METHOD OF MANUFACTURING THEREOF

PRIORITY

This application claims the benefit of U.S. Provisional Application No. 62/968,056, filed Jan. 30, 2020, and U.S. Provisional Application No. 63/070,704, filed Aug. 26, 2020, which are hereby incorporated by reference in their entirety for all purposes.

FIELD OF THE INVENTION

The present invention relates to medical devices and, more particularly, to bioresorbable implants such as wedge, bone void fillers and fixator implants. More specifically, such implants may be used for surgeries such as distal femoral osteotomy, high tibial osteotomy, pediatric osteotomies. Such implants can also be used for proximal humerus fractures, tibial plateau fractures, bone tumors and cyst, cancellous fractures, osteolysis total joints, and bone-soft tissue reconstruction.

BACKGROUND OF THE INVENTION

Hardware removal surgeries are among the most commonly performed surgical procedures. The corresponding nationwide figure accounting for orthopedic implant removal surgeries is 90 operations per 100,000 people per year in the USA only. Several studies have indicated pain and discomfort at the hardware site and impaired function to be the causes of removing the implant. Some studies have reported the complications of orthopedic hardware removal to be 24% to 50%.

Bioresorbable implants entered the market to eliminate the need for the follow-up removal surgeries of metal implants. Bioresorbable implants are arms of regenerative medicine that promote the restoration of the normal function of damaged tissues upon resorption of implants. Synthetic biodegradable polymers are considered the most commercially competitive polymers for these applications as they can be made in a cost-effective manner with a wide range of characteristics. Synthetic biodegradable polymers are also biocompatible, and may be used for the manufacturing of different medical devices, such as sutures, plate, bone fixation devices, stent, screws and tissue repairs, as their physicochemical properties are suitable for a broad range of medical applications. These implants aim for osseointegration.

Osseointegration is clinically defined as bonding of bone with surgical implants that induce the healing process of bone that involves tissue ingrowth from the broken ends without any intermediate fibrous tissue formation. Osseointegrated orthopedic implants are firmly immobilized within bone tissue. A common problem with bone implants is that vibration of the implants at the bony tissue can cause stress shielding, which leads to gradual resorption of the bone, which then leads to a loss in mechanical stability, and ultimately a complete failure of the implants. Implants using metals such as stainless steels, titanium-based alloys, and cobalt-chromium alloy may be particularly problematic, in that they have a tendency to cause stress shielding that may result in the mechanical instability of the bone-implant interface over time.

Several bioresorbable polymer devices have recently become available to create viable alternatives for some indications. As expected with evolving technology, solving one set of problems has engendered another. Despite initial promise, the unpredictable degradation profile and secretion of acidic by-product from current bioresorbable implants limited their fast-growing market penetration due to clinical complications. Bioresorbable implants have failed so far in providing excellent resorption and restoration profile as an ideal replacement due to the drawbacks of their common chemistry. The revision operations to remove the implants are increasing even more rapidly than those of primary repairs. The most common medical polymers used in bioresorbable implants, such as poly(lactic acid) (PLA) and poly (glycolic acid) (PGA) result in cyst formation (13.3-25.8%) and local inflammation (14-29%). 9 out of 10 current bioresorbable implants stay partially/completely intact within three years. Therefore, current bioresorbable implants do not improve the health outcomes compared with metallic implants due to the unpredictable process of resorption and consequently, lack of tissue integration.

BRIEF SUMMARY OF THE INVENTION

The present disclosure is related to a multi-component composite bioresorbable implant that enhances tissue integration.

Some embodiments of the invention are related to a three-part bioresorbable implant with inside-out resorption and excellent bone and tissue integration with an aliphatic polymer (e.g., for providing structural integrity), a bioresorbable natural carbohydrate filler that leaches out of the implant (e.g., to facilitate osseointegration), and a bone integrating mineral (e.g., to further facilitate osseointegration and thereby enhance bone tissue regrowth by providing adhesion sites for bone cells).

The aliphatic polymer can be poly (dl-lactic acid), poly (ε-caprolactone), poly(3-hydroxy butyrate), poly(butylene succinate), poly(propylene carbonate) or poly(propylene fumarate).

The bioresorbable carbohydrate filler can be cellulose, gelatin, alginate, oxygenated polyaromatic lignin or starch. The starch may be corn or maze. The bioresorbable carbohydrate filler can take the form of particles, fibers or whiskers. The bioresorbable carbohydrate can be in the size range of 5-30 µm.

The bone integrating mineral can be a ceramic such as calcium phosphate, hydroxyapatite, bioglass 45s5, or other suitable bone-integrating minerals. The bone integrating mineral can take the form of particles, fibers, or whiskers. The bone integrating mineral can be in the size range of 1-20 µm.

In some embodiments, the implant may be a four-part bioresorbable implant, with the fourth composition being an active agent, such as bone morphogenic proteins, cytokines, or other suitable enzymatic-based bone growth agents.

In some embodiments, the bioresorbable implant can have an implant state, where the bioresorbable natural carbohydrate filler leaches out of the implant over a period of 2 weeks to 6 months, and the ceramic assists in facilitating a secondary porous structure throughout the implant, for example, by providing adhesion sites for new bone cells. While in the implant state, the implant may cause cell and tissue growth from the interior of the implant.

The implant can take the form of wedges, bone void fillers, bone-soft tissue interface fixation implants, soft tissue fixation implants, or an implantable putty. For example, the implant can use thermal properties of the aliphatic polymer such that between, for example, the temperatures of 40-50° C., the implant is in a softened putty composition, and after implantation in the body, the implant may cure to a hardened state.

In some embodiments, the polymer of the implant may be porous. The porosity may be manufactured by means such as 3D printing, gas foaming, electrospinning or salt leaching. The pores may be in the size range of 50-400 μm. The porosity may be in the range of 10% to 90%.

Some embodiments of the invention are related to a bioresorbable implant with inside-out resorption and excellent bone and tissue integration with an aliphatic polymer providing structural integrity, a bioresorbable natural carbohydrate filler that leaches out of the implant, and a bone integrating mineral. The implant may have a pre-implant and post implant state, where the bioresorbable natural carbohydrate filler leaches out of the implant over a period of 2 weeks to 6 months while the implant is in a post-implant state. The implant may maintain structural load-bearing properties in the post-implant state even as it is gradually resorbing to provide for bone support to allow for adequate time for osseointegration as new bone tissue is regenerated. In some embodiments, the implant may still be load-bearing for at least 3 months to allow for sufficient bone growth and osseointegration. The aliphatic polymer may be porous to facilitate penetration and inside-out degradation and resorption.

In another aspect, the present disclosure is directed to a method of manufacturing a bioresorbable implant for orthopedic applications. The implant includes a synthetic aliphatic polymer matrix (Polymer A), a natural carbohydrate (Carbohydrate B), and a bone integrating component (Ceramic C). This scaffold enhances bone ingrowth and tissue integration utilizing an inside-out resorption mechanism disclosed herein to secure the manufacturing of bioresorbable implants in osteotomies and bone-soft tissue reconstruction surgeries.

Additionally, the present disclosure is directed to an optimized porous implant for load-bearing and non-load bearing orthopedic and soft tissue applications with optimum pore size, porosity and pore interconnectivity using fabrication methods such as gas foaming, 3D printing, electrospinning, and salt leaching.

Disclosed is a method of manufacturing bioresorbable implants in osteotomies and bone-soft tissue reconstruction surgeries independent of the choice of the materials. The inside-out resorption mechanism disclosed herein is to secure the manufacturing of bioresorbable implants that provide secondary osseointegration. The bioresorbable implant may be a tri-block composite, where each block may serve specific duties. The polymer A serves as a composite matrix chosen from an aliphatic polymer. The carbohydrate B serves as a fast-resorbable filler selected from natural bioresorbable carbohydrates. The ceramic C serves as a bone integrating element selected from minerals such as calcium phosphate, hydroxyapatite and bioglass 45s5.

It is to be understood that the method does not rely on the choice of any of the above components. The choice of the particular material for polymer A, carbohydrate B, and ceramic C presented in the examples herein should not be constructed as limitations on claims. The claims directed to the method of the present innovation should not be limited to the performances of any choice of materials from the presented polymer and/or ceramic family group.

The present disclosure builds upon technologies such as 3D printing and/or gas foaming to form the bioresorbable implant composite to serve its purpose of providing secondary osseointegration and tissue integration in bioresorbable implants such as osteotomies wedges, bone void fillers and soft tissue fixation implants like screws, rods and/or anchors with ultimately safe and timely resorption.

These and other embodiments, aspects and features of the present-disclosure are better understood from the following detailed description of the embodiments when read in conjunction with the appended drawings and figures.

DETAILED DESCRIPTION OF THE INVENTION

Described herein is a bioresorbable implant for use in osteotomies, bone-to-bone and bone-soft tissue reconstruction operations as a fixation implant, a bone void filler, and/or a wedge, where guided bone growth is achieved. The implant may include three blocks, each serving various roles in bone-tissue regeneration.

Figure 1A:
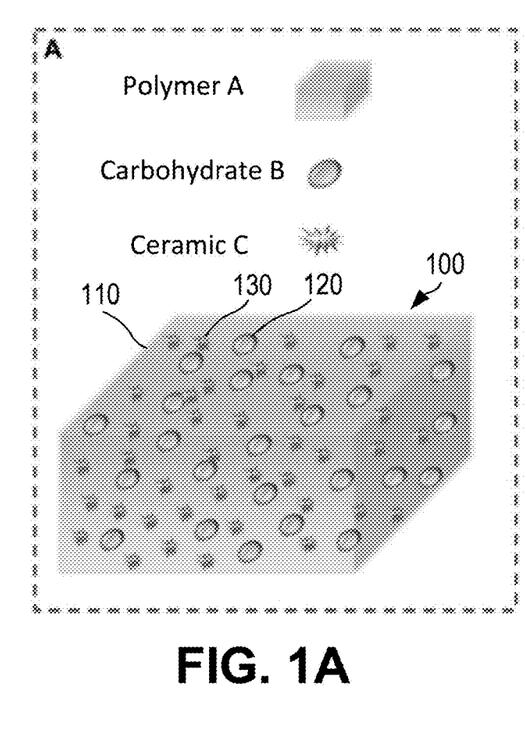
FIG. 1A is an illustration of a bioresorbable implant, according to embodiments.

FIG. 1A is an illustration of an example bioresorbable implant 100. In embodiments, the bioresorbable implant 100 may be a triblock composite. The illustrated bioresorbable implant 100 has three components: polymer A 110, carbohydrate B 120, and ceramic C 130. Polymer A provides structure to the bioresorbable implant 100. The structure as depicted is for illustration purposes, but it should be understood that the implant may take a multitude of structures beyond the cube as depicted, such as a disc, a square, an amorphous shape, a putty-like composition or otherwise. Further, the depiction of the implant as a triblock composite is intended to be non-limiting and the implant may be constructed of any number of components as is suitable. In the bioresorbable implant 100 of FIG. 1A, carbohydrate B 120 is distributed throughout polymer A 110. Ceramic C 130 is further distributed throughout polymer A 110.

Polymer A 110 may form an aliphatic polymer matrix providing structural integrity and mechanical strength. For example, polymer A may be an aliphatic polyester. In some embodiments, polymer A may be one or more of poly(dl-lactic acid), poly(ε-caprolactone), poly(3-hydroxy butyrate), poly(butylene succinate), poly(propylene carbonate) and/or poly(propylene fumarate)) and/or their copolymer such as poly(lactic-glycolic) acid including 10LA/90GA, 20LA/80GA, 25LA/75GA, 30LA/70GA, 40LA/60GA, 45LA/55GA, 50LA/50GA, 30LA/70GA and poly(ε-caprolactone and propylene carbonate) block copolymer.

In some embodiments, poly(propylene carbonate) (PPC) may be used as the polymer matrix. PPC may have enhanced tissue integration and resorption as compared to other biocompatible degradable polymer materials. Typically, other such polymers break down into acidic byproducts that decrease the pH of environment surrounding the implant site, resulting in inflammation and/or cyst formation, and generally slow down osseointegration and bone regeneration processes. For example, the most common medical polymers, poly(lactic acid) (PLA) and poly(glycolic acid) (PGA), result in cyst formation (13.3-25.8%) and local inflammation (14-29%). By contrast, PPC breaks down into non-acidic byproducts, i.e., water and $CO_2$, which do not have the same problems.

The carbohydrate B 120 may be a natural bioresorbable filler in shapes of particles, clusters, whiskers, and filaments in the size ranges of a micrometer and nanometer. The carbohydrate B 120 one or more of or combinations of the bioresorbable carbohydrates such as cellulose, gelatin, alginate, oxygenated polyaromatic lignin and/or starch (corn and/or maze). The carbohydrate B 120 may serve as a fast resorbable component creating pores inside the polymer A 110 matrix as the carbohydrate B 120 is resorbed (relatively quickly as compared to the polymer A 110 matrix). The created pores may allow for osseointegration as bone cells are able to penetrate and adhere to the implant within the pores. Additionally, these pores may provide a path for infiltration of water inside the scaffold for an inside-out resorption. Inside-out resorption refers to resorption that occurs, at least in part, from interior regions of the implant. Resorption may occur throughout the entirety of the implant. During inside-out resorption, water may infiltrate into interior regions of the implant and begins to degrade the implant from these interior regions as well as from the exterior of the implant (e.g., by breaking down and leaching out the carbohydrate B). As this occurs, tissue ingrowth into these interior regions may be further facilitated, as additional space is created for new tissue. This is markedly different from many conventional implants that merely allow resorption mainly inward from the exterior of the implant. An inside-out resorption mechanism is particularly advantageous, because it promotes faster osseointegration throughout the implant.

The cell adhesion property provided by carbohydrates may be especially important in embodiments employing a polymer A 110 matrix of hydrophobic polymers (e.g., PPC), because such polymers tend to repel cell adhesion. The incorporation of carbohydrates as a filler within the polymer A matrix (e.g., where the polymer A 110 is PPC) may serve to counteract this effect.

In embodiments, the ceramic C 130 may be microparticles of a bone integrating mineral compound providing bioactivity and bone regeneration capabilities. The ceramic C 130 may be at least one of or a combination of the bone integrating compounds such as calcium phosphate, hydroxyapatite and bioglass 45s5. The presence of at least one or a combination of bioactive minerals as ceramic C 130 provides for enhanced bone integration and osteoblast cell penetration and growth after implantation, for example, by providing adhesion sites for new bone cells. The weight percentage of ceramic C 130 can be in a range of 1 wt %, 2.5 wt %, 5 wt %, 7.5 wt %, 10 wt %, 12.5 wt %, 15 wt %, 17.5 wt %, 20 wt %, 25 wt % and 30 wt %.

Any suitable combination that includes a polymer A 110 as described above, a carbohydrate B 120 as described above, and a bone-integrating mineral (ceramic C 130) as described above may be used to create a suitable implant according to embodiments. For example, an embodiment of an implant for excellent bone resorption may be made of poly(propylene) carbonate to provide for the matrix structure of the implant, with a starch filler, and bioglass 45s5. The described PPC-starch-bioglass implant may have a pre-implant state where the PPC has a manufactured porosity with the starch occupying regions throughout the PPC matrix and the bioglass dispersed. In some embodiments, the implant may be pre-formed into disks, rods, wedges, screws, wires, or any suitable shape for implantation into an implant site, as will be described in further detail below (e.g., with respect to FIGS. 6A-8).

The mechanism of the inside-out degradation is based partly on the presence of carbohydrate B filler inside the structure of the polymer A matrix. In such embodiments, the amount of carbohydrate B regulates the degradation time. The presence of as low as 1 wt % to 10 wt % results in a low degradation profile. However, the presence of 50 wt % of carbohydrate B produces a fast resorbable implant. The carbohydrate B weight percentage can be in a range of 1 wt %, 3 wt %, 5 wt %, 10 wt %, 15 wt %, 20 wt %, 25 wt %, 30 wt %, 35 wt %, 40 wt %, 45 wt %, and 50 wt %, depending on the desired degradation profile.

In some embodiments, the implant may maintain structural load-bearing properties in the post-implant state even as it is gradually resorbing to provide for bone support to allow for adequate time for osseointegration as new bone tissue is regenerated. In some embodiments, the implant may still be load-bearing for at least 3 months to allow for sufficient bone growth and osseointegration.

The carbohydrate B 120 may degrade by bulk erosion as water flows into the implant. Bulk erosion allows for degradation throughout the entire implant, allowing for greater integration of bone tissue deeper into the implant.

Figure 1B:
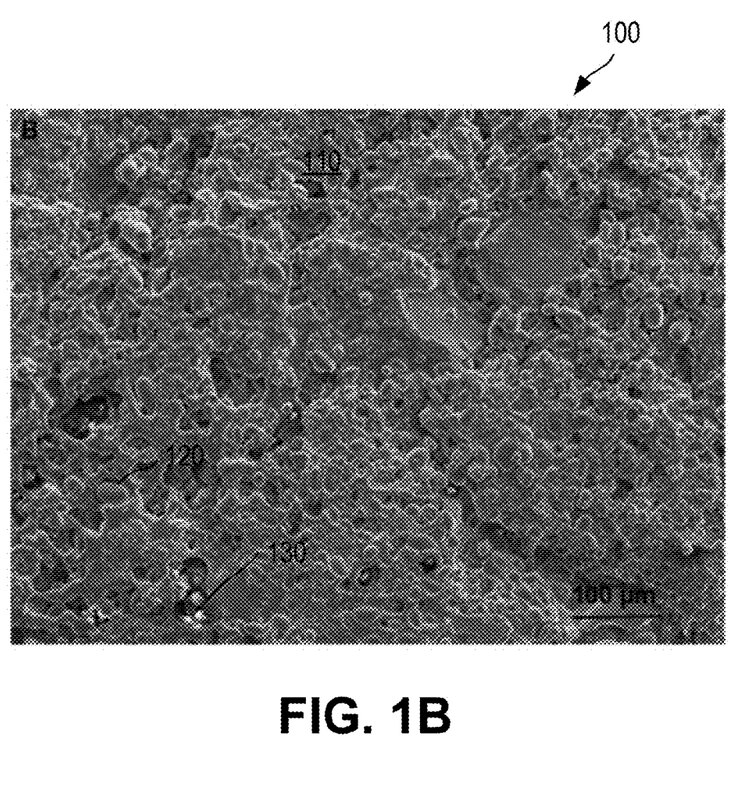
FIG. 1B is an scanning electron microscope (SEM) image of a bioresorbable implant showing a polymer, carbohydrate, and ceramic, according to embodiments.

FIG. 1B shows an SEM image of the bioresorbable implant 100 displaying the polymer A 110, carbohydrate B 120 and ceramic C 130 produced in accordance with an embodiment of the present disclosure. The SEM image was captured using Zeiss EVO 50 SEM, operating at an acceleration voltage of 10 kV. The cross-section of samples was mounted on aluminum stubs, using conductive silver paint, and then gold-sputtered (Emitech K550X sputter coater) prior to SEM analysis.

In embodiments, the implant may incorporate an active agent as a fourth component. The active agent may be a bioactive compound that further enhances bone growth. The active agent may be dispersed throughout the implant. This active agent may be bone morphogenic proteins (BMPs), cytokines, or suitable chemicals that enzymatically promote bone growth. Such active agents may further promote bone growth by, for example, causing the body to create a flux of ions necessary for bone growth such as calcium, sodium, potassium, and phosphate. In embodiments, the active agent may be antibiotics such as gentamycin or vancomycin or anti-inflammatory drugs such as dexamethasone) and a galectin-3 inhibitor to avoid and minimize inflammation and infection. The active agent may be one of, or any combination of the bioactive compounds described above.

Figure 2A:
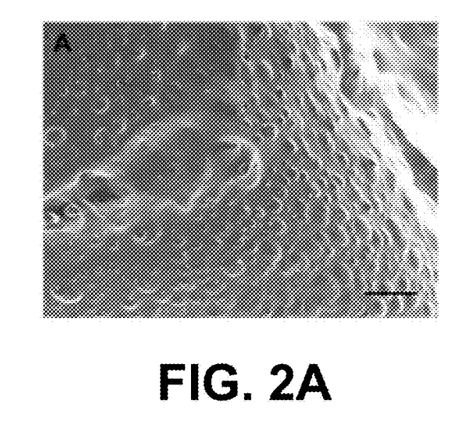
FIGS. 2A-2C are SEM images of different bioresorbable implants with varying weight percentages, according to embodiments.
Figure 2B:
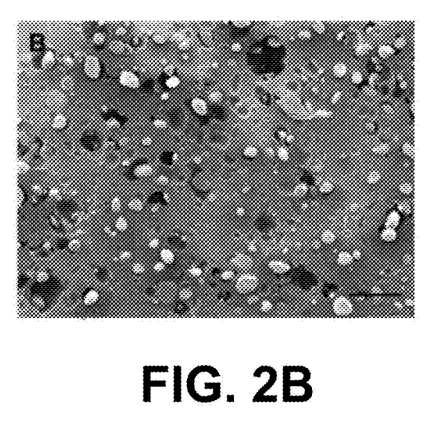
Figure 2C:
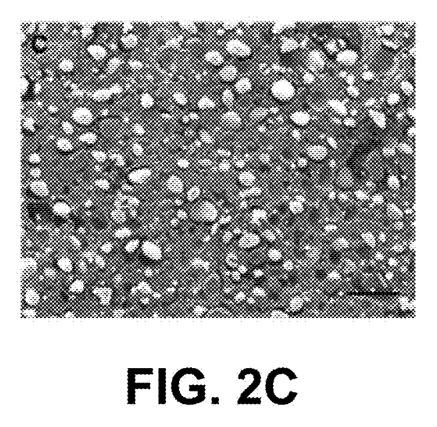

FIGS. 2A-2C show SEM comparisons of the inside-out resorption mechanism with implants having differing weight percentages of carbohydrate B. The SEM photos showing the implants after 8 weeks of incubation in a simulated body fluid at 37° C. in a dynamic environment. The SEM images were captured using Zeiss EVO 50 SEM, operating at an acceleration voltage of 10 kV. The cross-section of samples was mounted on aluminum stubs, using conductive silver paint, and then gold-sputtered (Emitech K550X sputter coater) prior to SEM analysis.

FIG. 2A shows an example implant with 0 wt % carbohydrate B resulting in slow resorption. Observations of the implant in use demonstrate that without the additional voids formed from carbohydrate B leaching out of the structure of polymer A, cells and tissue have a difficult time reaching the interior of the implant to facilitate inside-out growth.

FIG. 2B shows an example implant with 25 wt % carbohydrate B. Such an implant would have a moderate resorption rate.

FIG. 2C shows an example implant with 50 wt % carbohydrate B. Due to the higher percentage of resorbable carbohydrate B, the degradation profile of the implant is much higher, as a larger weight percentage of the implant leaches out over time. The SEM photos showing the implants after 8 weeks of incubation in a simulated body fluid at 37° C. in a dynamic environment. The SEM images were captured using Zeiss EVO 50 SEM, operating at an acceleration voltage of 10 kV. The cross-section of samples was mounted on aluminum stubs, using conductive silver paint, and then gold-sputtered (Emitech K550X sputter coater) prior to SEM analysis.

In FIGS. 2B-2C, the dashed lines indicate areas of leaching, providing a porous scaffold. Upon the infiltration of water and body fluids, the hydrolysis degradation starts from inside the bulk of the samples.

Figure 3:
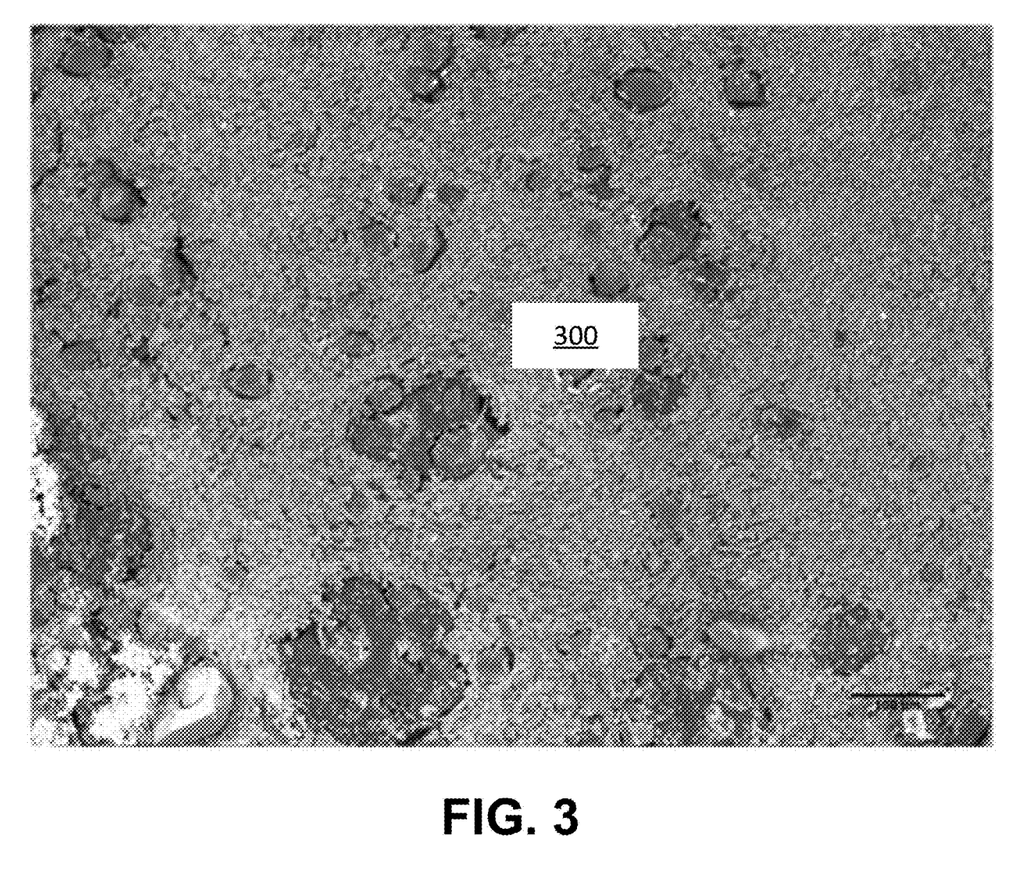
FIG. 3 is an SEM micrograph of a surface of bioresorbable implant, covered by bone cells.

FIG. 3 displays an SEM micrograph of the surface of a bioresorbable rod 300 having an aliphatic polymer matrix (polymer A), a natural bioresorbable carbohydrate filler (carbohydrate B) and a bone mineral agent (ceramic C) seeded with human osteoblast cells. A layer of attached cells rests on top of the scaffold while the cells were guided to stick to the matrix and not the fast resorbable filler. The guided osteoblast and bone cell attachment and proliferation are used as a way to open pores for leaching the carbohydrate B out. This allows cells to penetrate and infiltrate inside the bioresorbable implant providing guided inside-out tissue ingrowth from the bulk of the implant.

Surface morphology was examined by Zeiss EVO 50 SEM, operating at an acceleration voltage of 10 kV. The cross-section of samples was mounted on aluminum stubs, using conductive silver paint, and then gold-sputtered (Emitech K550X sputter coater) prior to SEM analysis. SEM analysis was used to examine the cell morphology of the osteoblast cells on the surface of scaffolds within 24 h post-culture. For this analysis, the samples were placed in 24 well-plates, and 75 µL of cell suspension was added to each well to have 2×105 cells/well. The attached cells were fixed in 2.5% glutaraldehyde for 1 h and washed with PBS for at least three times. Bioresorbable disks incubated at room temperature for another hour in the secondary fixative (1% osmium tetroxide in 0.1 M PBS). Sequential dehydration in various ethanol grades including 30, 50, 70, and 90% and pure ethanol were then performed. The ethanol residues were removed from the samples by using 0.5 mL of hexamethyldisilazane (HMDS) and incubation at room temperature for 2 min. Subsequently, the samples were dried in a desiccator with the lid off to allow the HMDS to evaporate overnight. The gold coating was used for the final SEM analysis.

Figure 4A:
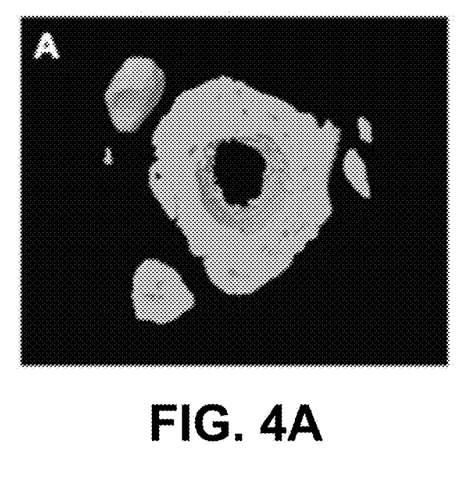
FIGS. 4A-4C is a series of chronological Microcomputed Tomgoraphy (MicroCT) time-lapse images of a bioresorbable implant in a rat with a femoral head defect, according to embodiments.
Figure 4B:
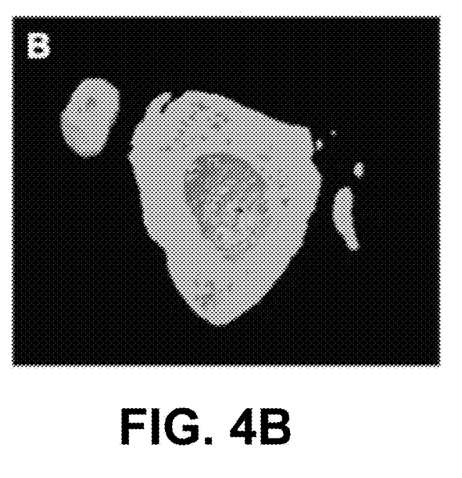
Figure 4C:
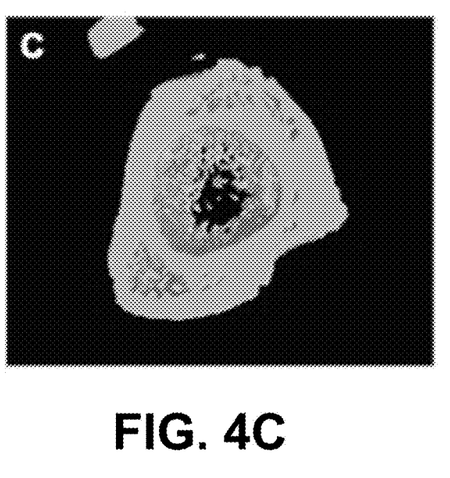

FIGS. 4A-4C show a chronological MicroCT image of the pre-implant, implant, and post-implant in the femoral head of rats, according to embodiments. The implant of FIGS. 4A-4C is a triblock composite for facilitating bone regeneration, produced in accordance with the embodiments of the present disclosure. The polymer A was selected from an aliphatic polymer such as polycaprolactone and/or polypropylene carbonate, carbohydrate B was a choice of natural resorbable carbohydrates such as cellulose and/or alginate and a bioactive mineral agent such as hydroxyapatite and/or calcium phosphate was used to enhance bioactivity and bone regrowth. The rods were implanted in 15+ weeks old male Wistar Rats (Animal Resources Centre) in a femoral head defect to simulate a distal femoral head osteotomy. The rod was implanted for 12 weeks. The designed inside-out degradation mechanism was effective in encouraging new tissue to form inside the structure of the implants as early as 12 weeks post-implantation.

FIG. 4A shows a femoral head defect, which was created in a femoral head of a rat to simulate a distal femoral head osteotomy. The femoral head defect was then implanted with a bioresorbable implant, such as the bioresorbable implant 100. FIG. 4B shows the femoral head defect of FIG. 4A with an implanted bioresorbable implant (e.g., the bioresorbable implant 100) in the form of a rod. FIG. 4C illustrates the same area 12 weeks after implantation. As can be seen, bone-growth can be observed, with the fill-in of tissue extending past the initial defect boundary. Moreover tissue growth can be seen in the interior region, past the boundary line of the exterior of the implant, signaling tissue growth within the implant.

Bioresorbable rods and/or wedges for osteotomies and/or soft-hard tissue interface reconstruction of FIGS. 4A-4C were scanned at an isotropic voxel resolution of 14 µm with a 0.5 mm aluminum filter, 50 kV X-ray tube voltage, 800 uA tube electric current, and 4500 ms scanning exposure time. A cutoff for mineralized tissue of 0.3 g cm$^{-3}$ mineral was used for 3D reconstruction using NRecon software. Although FIGS. 4A-4C reflect the implantation of the bioresorbable implant in a particular location for a particular procedure, the disclosure contemplates a similar implantation in any suitable location for any suitable procedure to yield similar results.

The implants disclosed herein exhibit multiphase osseointegration. For example, the implants allow for a two-phase osseointegration process. In this example, a primary osseointegration occurs as cells and body fluids penetrate pores in the implant (which may start out as a porous structure). The porosity of the implant allows for inside-out resorption from the very beginning. As the implant degrades while in the body (initially mostly by the leaching out of carbohydrate B, but also by the slower degradation of polymer A), additional pores are created. These additional pores set the stage for a secondary osseointegration, allowing for additional cell penetration. The additional pores also allow the ingress of additional body fluids, thereby increasing degradation of the implant, which again allows for additional cell penetration. In this way, the implant increasingly allows inside-out resorption as it degrades. Tunability of the degradation profile allows for control over the speed at which secondary osseointegration begins and proceeds.

The additional pores also allow for enhanced vascularization and connective tissue growth. Thus, the providing for enhanced bone integration as well as efficacious healing.

Some embodiments may use a porous structure within the implant to facilitate enhanced tissue regeneration. In such embodiments, the porous structure inside a bioresorbable implant composed of polymer A, carbohydrate B and ceramic C can be formed using 3D printing, electrospinning, salt leaching and/or gas-foaming. Aliphatic polymers such as PLA, PLGA, and PCL are soluble in carbon dioxide providing the chance of using gas foaming to form porosity.

Figure 5:
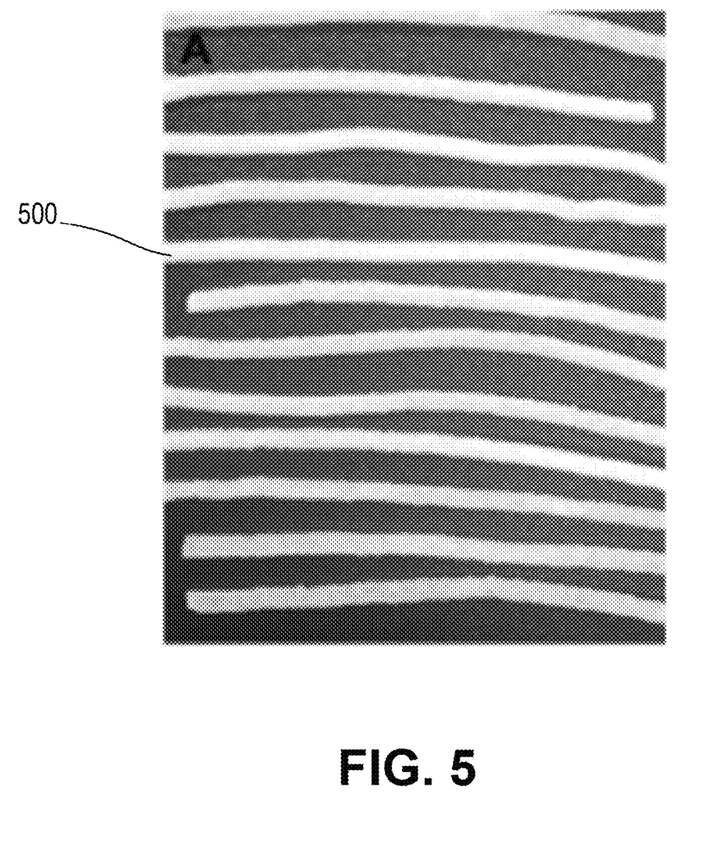
FIG. 5 shows examples of implant composites that have been extruded as filaments to be used in 3D printing a bioresorbable implant, according to embodiments.

FIG. 5 shows example bioresorbable implant composites that have been 3D printed according to embodiments. FIG. 5 shows an overall uniform pattern achieved by 3D printing with an extruded filament. In this embodiment, a single screw extruder was used with the die temperature ranging from 125° C. to 210° C. depending on the type of the polymer A. 3D printing may achieve a pore size of 100 µm to 150 µm with the porosity ranging from 10% to 90%.

Figure 6A:
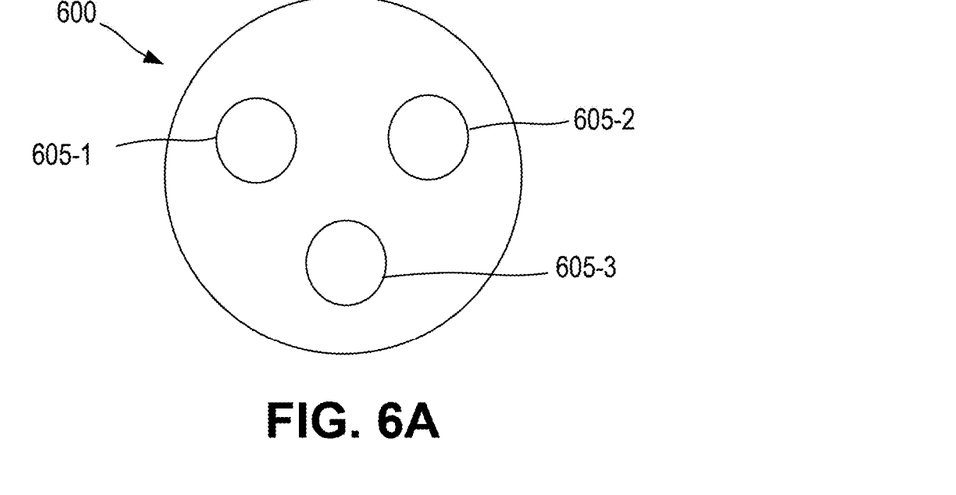
FIGS. 6A-6C illustrate the step-by-step formation of a porous bioresorbable implant using a gas foaming technique.
Figure 6B:
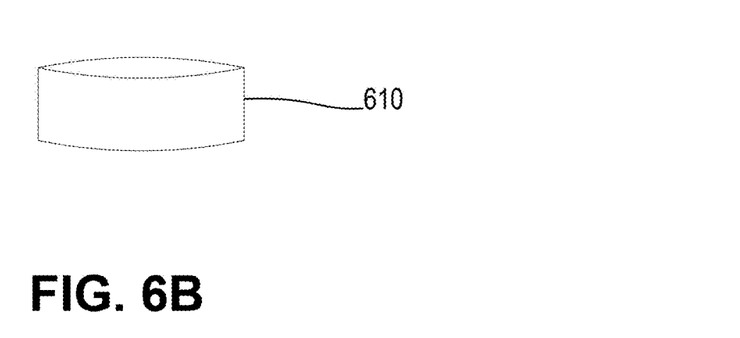
Figure 6C:
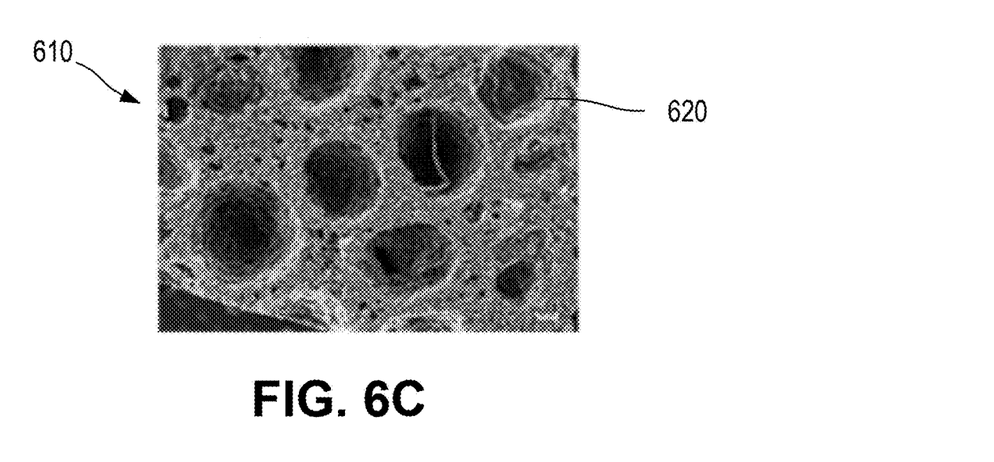

FIGS. 6A-6C shows the steps to form an embodiment of a gas-foamed bioresorbable implant (e.g., the bioresorbable implant 100) in accordance with the present disclosure. Gas foaming may be an efficient technique to generate uniform pores.

FIG. 6A shows a custom mold 600 for forming a bioresorbable implant. The mold assembly may include one or more mold templates (e.g., the mold templates 605-1, 605-2, and 605-3). The bioresorbable implant can be made within these mold templates by any suitable methods (e.g., by pouring in a mixture). The custom mold 600 may have any number of mold templates (e.g., one, two, three, four, or more) to form a number of bioresorbable implants. Each of the mold templates may have any suitable shape to output a desired implant. For example, the mold templates may be configured to output a disk-shaped implant, a wedge-shaped implant, a rod-shaped implant, or any other suitable implant.

In some embodiments, the custom mold 600 may be filled with a mixture for forming the composite bioresorbable implant, and then placed in a pressure chamber for gas foaming. The pressure chamber for forming bioresorbable disks, rods, wedges, screws and wires can be a high-pressure vessel (such as Thar, 100 mL view cell). Prior to pressuring the vessel, a desired temperature such as Ts of 25, 30 and 40° C. may be set using the Thar reactor temperature controller. The system may be pressurized with $CO_2$ to a predetermined pressure such as Ps of 50, 75 and 125 bar using a syringe pump (e.g., ISCO, Model 500D) and the pump may then run at constant pressure mode. After a desirable time such as 1, 2 4 and 12 h, the temperature can be gradually decreased to room temperature, and the system depressurized at a predetermined depressurization rate such as DPR of 0.2, 2.5 and 10 bar/s.

FIG. 6B shows an example implant 610 (a disk-shaped implant) formed by the above process from the custom mold 600. FIG. 6C shows a close-up photograph of the implant 610. As can be seen, the implant 610 is a porous structure, with pores 620 throughout the structure. These pores can be achieved by utilizing a gas-foaming process to extrude the structure of the implant.

Figure 7A:
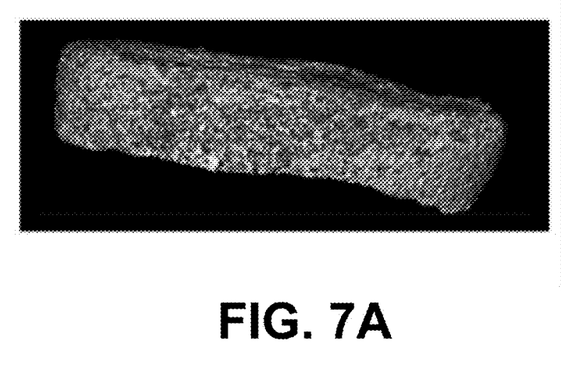
FIGS. 7A-7B are MicroCT images of pore distribution in a bioresorbable implant, according to embodiments.
Figure 7B:
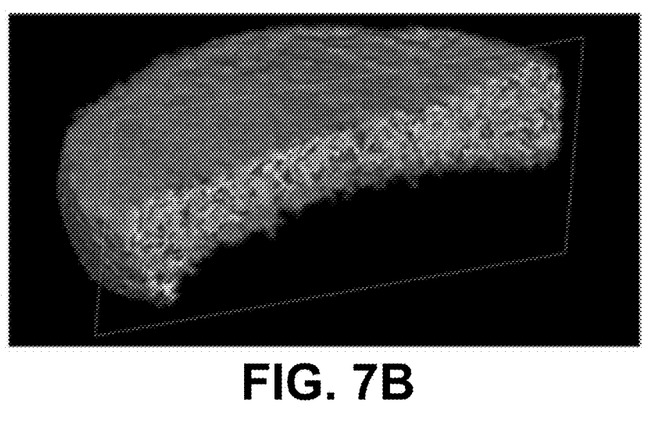
Figure 8A:
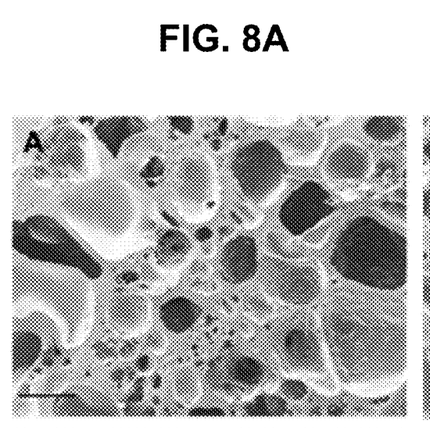
FIGS. 8A-8D are SEM images of bioresorbable implants with varying porosity, according to embodiments.
Figure 8B:
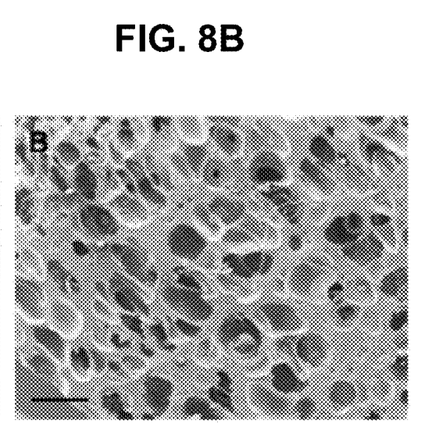
Figure 8C:
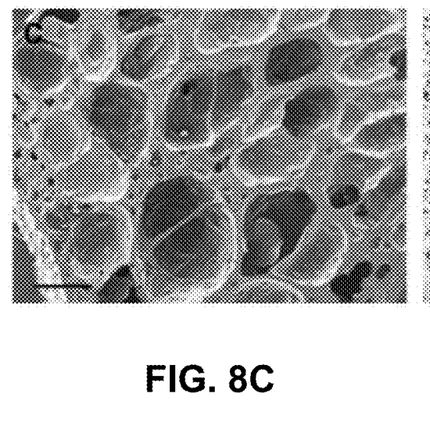
Figure 8D:
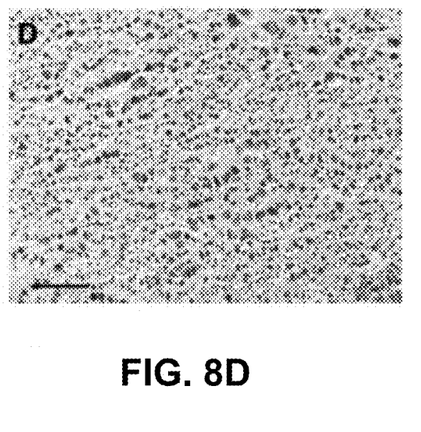

FIG. 7A-7B shows different views of a MicroCT image analyzing pore distribution and overall porosity in a sample slice. In assessing the pore distribution and porosity, temperature, pressure, depressurization rate and soaking time were optimized for each sample based on the solubility of the used aliphatic polymer solubility in carbon dioxide. The subcritical, critical and supercritical points were extracted from the Pressure-Temperature phase diagram of $CO_2$. This may generate porosities in the range of 20% to 75% and the pores may be uniformly distributed towards the bulk of bioresorbable implants in order to provide excellent bone integration.

The porous bone integrated bioresorbable implants were further analyzed by Micro-Computed Tomography (MicroCT). Specimens were scanned with a microfocus X-ray source using Skyscan 1072 (Bruker MicroCT). During scanning, the specimen was rotated in small increments over 360° C., and an X-ray projection image was captured at each step. The reconstructed images were acquired using Avizo® 3D software to analyze the 3D porous structure and the interconnectivity of the pores.

FIGS. 8A-8D show various embodiments of a bioresorbable implant with varying porosity, based on different gas-foaming parameters. The various porous structures may be achieved by the alteration of temperature and pressure. In some embodiments, the porous structures may have sizes in the range of 50 µm to 400 µm. In some embodiments, an implant (e.g., the bioresorbable implant 100) may have a porosity in the range of 10% to 90% porosity.

The pore size of the gas foamed samples was measured by Scanning Electron Microscopy Energy-Dispersive X-ray Spectroscopy (SEM-EDS). Samples were mounted on aluminum stubs, using conductive silver paint, and then gold-coated using an Emitech K7550X instrument. SEM analysis was conducted using a Zeiss EVO 50 SEM, operating at an acceleration voltage of 10 kV. Images were analyzed using ImageJ software (National Institutes of Health, USA). The SEM apparatus was also fitted with a LaB6 filament and EDS measurements were made using an iXRF Iridium Ultra EDS system.

Figure 9A:
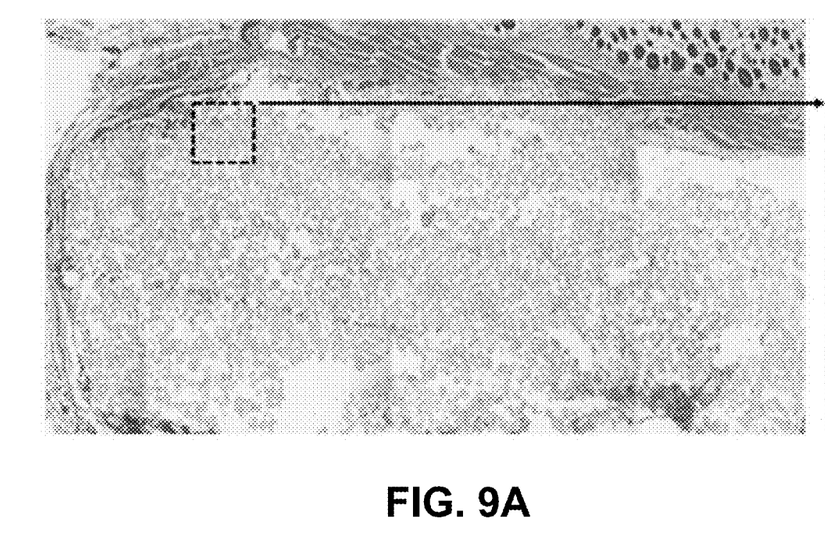
FIGS. 9A-9B are Haemotoxylin and Eosin (H&E) histology images of a skin treated with a porous bioresorbable implant, according to embodiments.
Figure 9B:
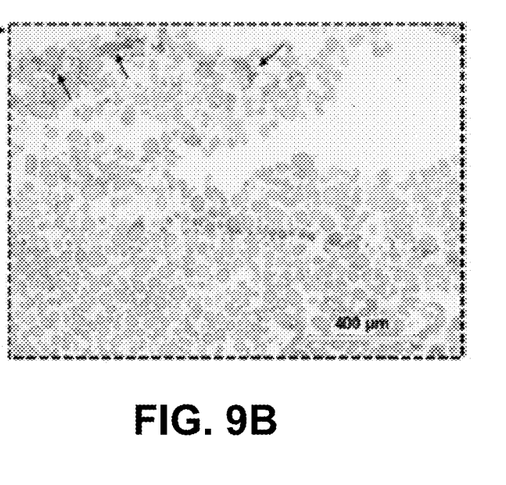

FIG. 9 shows Haemotoxylin and Eosin (H&E) histological photographs of skin treated with porous bioresorbable disks. In an H&E stain, cell nuclei and cytoplasm are stained with typically blue and pink dyes, respectively.

The bioresorbable disks of FIG. 9 were implanted into mice to observe tissue regeneration. The tissue regeneration was observed as early as two weeks post-implantation. A mouse model of subcutaneous implantation was used to evaluate the filtration of tissues to the porous scaffolds. Porous disks (5 mm diameter and 3 mm in height) were prepared under aseptic conditions and manipulated in a sterile laminar hood prior to implantation. Pathogen-free, male BALB/c mice, aged 12-14 weeks and weighing 27±1.9 g, were purchased from the Australian Animal Resources Centre. All animals were acquired, housed and studied under a protocol approved by Sydney Local Health District (SLHD) Animal Welfare Committee in Sydney, Australia. Each mouse was anesthetized individually by intraperitoneal injection of a mixture of ketamine (50 mg/mL) and xylazine (50 mg/mL) in a volume of 0.01 mL/g of body weight. The dorsal hair was shaved, and the skin was cleaned with betadine solution and washed with sterile saline.

Two incisions of about 1 cm in length were made on the dorsal area and dissected to create a subcutaneous pouch into which the porous scaffolds were inserted. All wounds were sutured and covered using Atrauman® (Hartmann, Australia) and IV3000 wound dressings (Smith & Nephew) for 7 days. Carprofen (5 mg/kg) was given at the time of anesthesia and then on the following day post-surgery for analgesia. After surgery, each mouse was caged individually for the first two days and then three mice per cage after that with free access to water and food.

Samples were then obtained using recognized scientific protocols. Skin biopsies were collected for histological analysis 2 weeks post-implantation. Skin biopsies obtained at each time point were fixed in 10% (w/v) formalin for 24 h, tissue processed and embedded in paraffin. 5 µm sections were deparaffinized in xylene and stained with hematoxylin and eosin for histological analysis. FIG. 9 illustrates a photograph of such a biopsied sample.

In addition to solid implants, other forms of implants may be used, and particularly adapted for different procedures. For example, in some embodiments, an implant may be a putty material in a pre-implant state. Any suitable composition, such as a three-part composition including a polymer, a carbohydrate, and a bone-integrating mineral as discussed above may be used (alternatively, a four-part composition may be used, which may include an active agent). In some embodiments, the implant may use PPC as Polymer A for forming the polymer matrix. In some embodiments, the implant may be composed of PPC, a starch carbohydrate filler, and bioglass 45s5 ceramic.

In these PPC implants, the PPC forms a porous matrix to provide structural integrity and load-bearing properties to the PPC implant upon implantation. The starch filler is dispersed throughout the matrix, such that upon erosion, the PPC implant is further opened up for secondary osseointegration with bone tissue and provide for inside-out resorption of the PPC implant. The bioglass 45s5 ceramic is dispersed throughout the PPC implant to facilitate cell adhesion.

In some embodiments, the PPC implant composition may be such that it can be brought to a putty state prior to implanting, and then caused to harden in a post-implant state after molding the PPC implant to a desired conformation. In these embodiments, prior to implantation, while the PPC implant is still in a pre-implant state, the PPC implant may be heated to a temperature between 40° C. and 50° C. The thermal properties of PPC may allow the PPC implant to become putty-like prior to implantation at a much lower temperature than implants using a matrix formed of other polymers. For example, an implant with a PPC matrix may be in a moldable putty state at temperatures as low as between about 40° C. to 45° C. to allow for both ease of handling by the surgeon without having to wear bulky thermal protection equipment and to allow implantation without causing thermal damage to the patient around the implant site.

The PPC implant can be heated to a softening temperature of about 40° C. to 50° C. in order to obtain a putty-like consistency. While in this state, due to the lower heated temperature to obtain a putty-like consistency, a surgeon may be able to easily handle the PPC implant without the detriments of heat causing inaccuracy and mistakes in implantation. Furthermore, the lower heat differential between the PPC implant and resting body temperature allows for easier implantation without causing the patient discomfort due to excessive heat from the PPC implant. Preferably, the softening temperature may be between about 40° C. to 45° C., to allow for the most comfortable handling of the putty implant.

Upon implantation, the putty-like consistency of the PPC implant can cure and harden at approximately the body's natural temperature of about 37° C. As the PPC implant hardens, the structural integrity provides load-bearing properties throughout the PPC implant to strengthen and support the implant site throughout recovery. Moreover, even as the filler degrades, the PPC implant maintains load-bearing qualities. More information about the load-bearing capabilities of PPC can be found in "Reinforced Poly(Propylene Carbonate) Composite with Enhanced and Tunable Characteristics, an Alternative for Poly(lactic Acid)," *Applied Materials & Interfaces* (2015), which is incorporated herein by reference in its entirety for all purposes.

After implantation, the PPC implant may enter a hardened post-implant state. In the post-implant state, the matrix of the PPC implant may cure at the body's temperature of around 37° C. to form a hardened, load-bearing structure. In the post-implant state, within a period of 2 weeks to 6 months, the starch degrades by bulk erosion as water enters and flows through the PPC implant. While the carbohydrate degrades from the PPC implant, the matrix may support and bear load in order to facilitate enhanced bone tissue regrowth throughout the PPC implant. The ceramic may form adhesion sites on the PPC matrix as well as further enhance bone tissue regrowth. The starch may further facilitate cell adhesion within the PPC matrix, allowing for an inside-out resorption effect.

The particular temperature profile described immediately above, where the PPC implant is in a putty state at temperatures between about 40° C. to 45° C. and in a hardened, load-bearing, post-implant state at body temperature (e.g., around 37° C.) is made possible by the use of PPC as the polymer matrix. Such a temperature profile would not be possible using more conventional polymers such as PLA or PGA. Furthermore, as discussed in greater detail above, PPC may facilitate greater resorption and cause less stress to the body during recovery due to PPC's breakdown over time into non-acidic, non-harmful byproducts. This may aid in patient recovery and also reduce the need for revision operations due to pain from acidic byproducts. Although the disclosure focuses on implant putties based on PPC, the disclosure contemplates that any suitable polymer may be used as Polymer A in an implant putty.

Figure 10A:
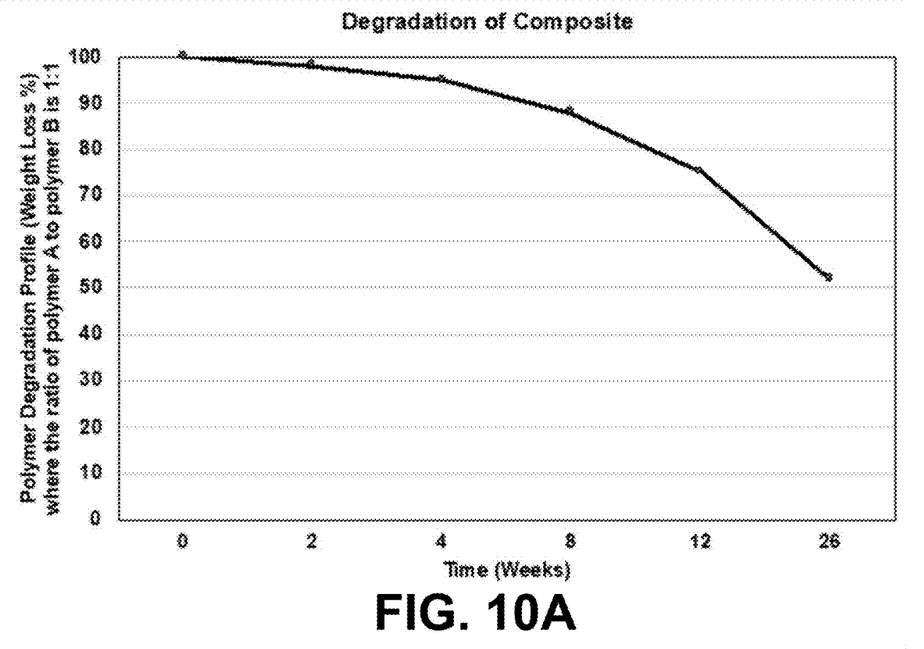
FIGS. 10A-10B show graphs of degradation profiles of a bioresorbable implant, according to embodiments.
Figure 10B:
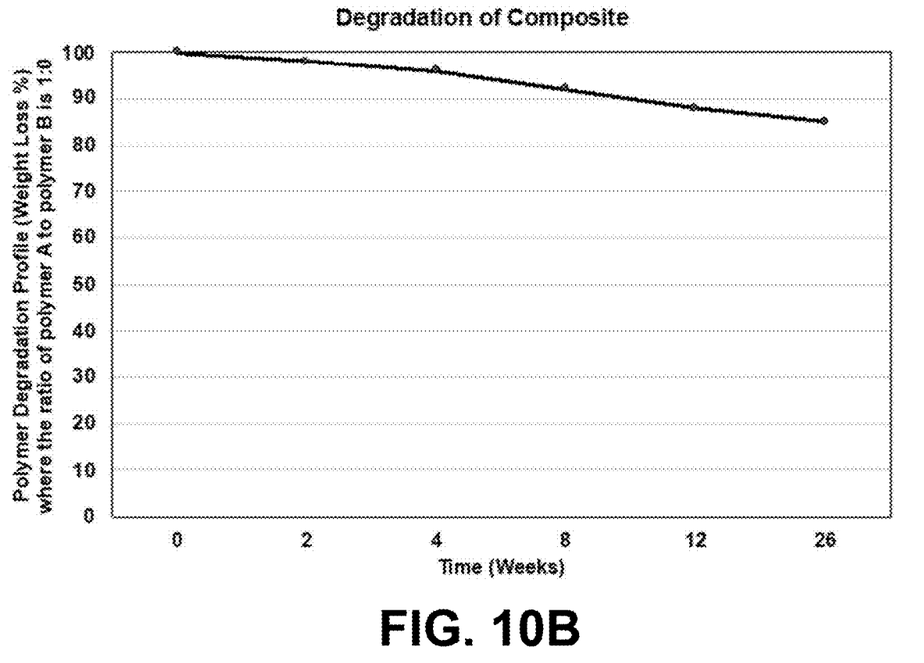

FIGS. 10A-10B show graphs comparing the degradation profiles of bioresorbable implant composites with two different ratios of polymer A to carbohydrate B. The degradation profile experiment reflected by these graphs was done in simulated body fluid saturated with lipase and α-amylase enzymes to simulate body fluid environment over the course of 26 weeks. The degradation is measured with respect to weight loss percentage over the course of the 26 weeks.

FIG. 10A shows the degradation profile of a bioresorbable implant composite with a ratio of 1:1 between polymer A and carbohydrate B. FIG. 10B shows the degradation profile of a bioresorbable implant composite with a ratio of 1:0 between polymer A and carbohydrate B. That is, the graph in FIG. 10B reflects data associated with a composite that does not include any amount of the carbohydrate B. On comparing these two graphs, it is evident that the degradations of the two composites (as indicated by the weight loss percentage) remain similar until approximately the 4-week mark, at which point, the composite of FIG. 10A (which includes carbohydrate B) degrades faster than the composite of FIG. 10B (which does not include carbohydrate B). The 4-week mark may be around the time that carbohydrate B begins leaching out of the composite of FIG. 10A, creating a secondary porous structure, as explained in further detail above. This may lead to further osseointegration and ingress of body fluid, which leads to further degradation. As seen in FIG. 10B, the effects are compounded over time, resulting in an accelerated degradation profile where the composite degrades at an increasingly faster rate.

The faster degradation of the bioresorbable implant with the addition of carbohydrate B, as opposed to just the presence of polymer A, may allow for bones to begin bearing weight at an earlier point. Having the bones gradually bear weight as the implant degrades allows for a more gradual return to bone strength and bone healing, as opposed to the implant of only polymer A in FIG. 10B, which degrades much more slowly, and as a consequence, prevents the bones from bearing weight to facilitate faster bone healing and bone strength. As explained above, the degradation profile is highly tunable, such that an optimal composite may be formed to allow a bone structure to bear increasing amounts of weight at an optimal rate without overloading it. For example, the degradation profile may be tuned by adjusting the ratio of Polymer A to Carbohydrate B.

Figure 11:
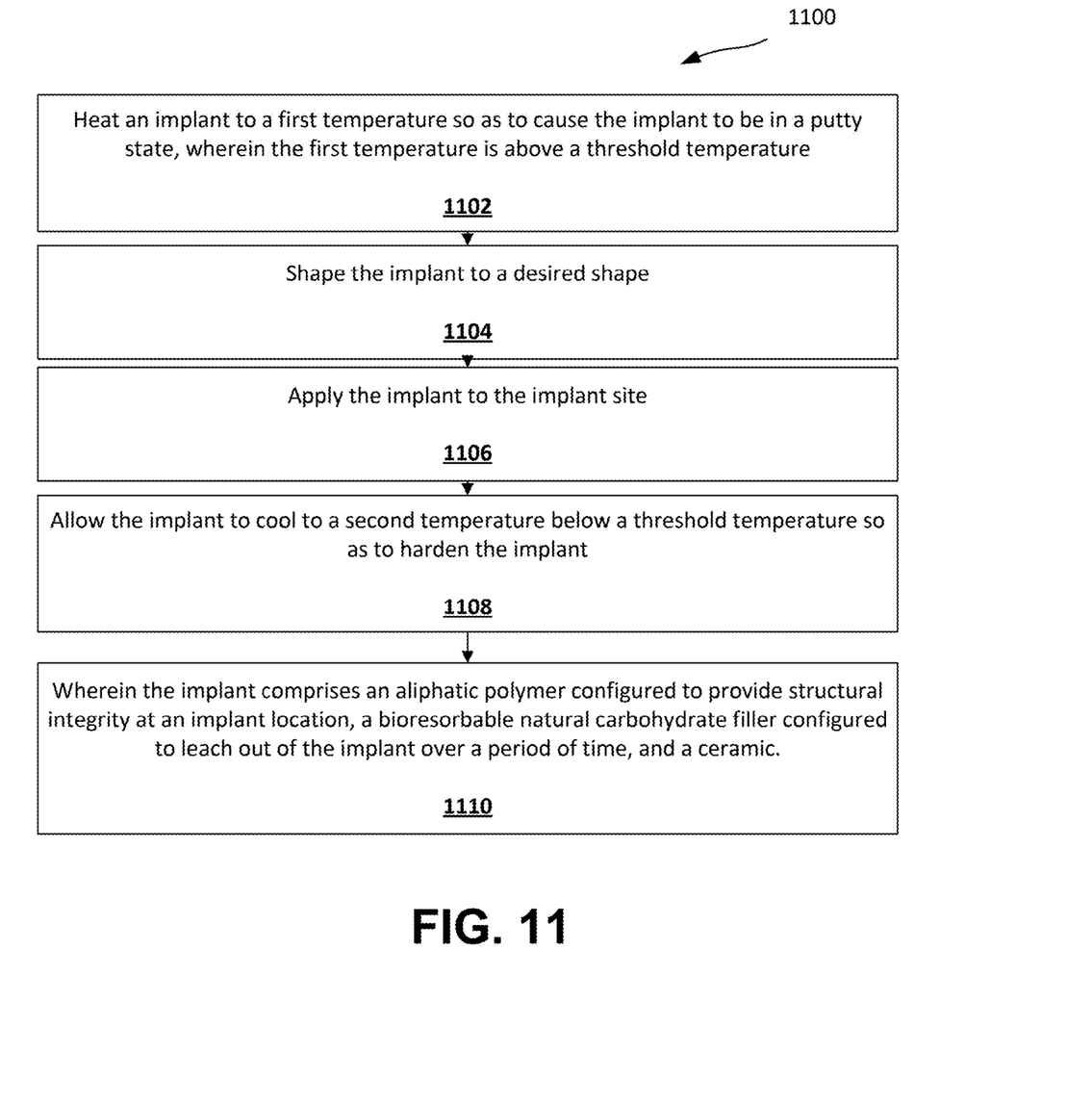
FIG. 11 shows a method of implanting a bioresorbable implant, according to embodiments.

FIG. 11 illustrates an example method 1100 for implanting a bioresorbable putty implant into an implant site on a bone of a patient. The method may include, at step 1102, heating an implant to a first temperature, so as to cause the implant to be in a putty state, wherein the first temperature is above a threshold temperature. At step 1104, the method may include shaping the implant to a desired shape. At step 1106, the method may include applying the implant to the implant site. At step 1108, the method may include allowing the implant to cool to a second temperature below threshold temperature, so as to harden the implant.

In some embodiments, the implant in example method 1100 may be composed of an aliphatic polymer, a bioresorbable carbohydrate filler, and a ceramic, such as the bioresorbable implant 100.

Particular embodiments may repeat one or more steps of the method of FIG. 1100, where appropriate. Although this disclosure describes and illustrates particular steps of the method of FIG. 1100 as occurring in a particular order, this disclosure contemplates any suitable steps of the method of FIG. 1100 occurring in any suitable order. Moreover, although this disclosure describes and illustrates an example method for implanting a bioresorbable putty implant into an implant site on a bone of a patient, including the particular steps of the method of FIG. 1100, this disclosure contemplates any suitable method for implanting a bioresorbable putty implant into an implant site on a bone of a patient, including any suitable steps, which may include all, some, or none of the steps of the method of FIG. 1100, where appropriate. Furthermore, although this disclosure describes and illustrates particular components, devices, or systems carrying out particular steps of the method of FIG. 1100, this disclosure contemplates any suitable combination of any suitable components, devices, or systems carrying out any suitable steps of the method of FIG. 1100.

Although specific embodiments of the invention have been described, various modifications, alterations, alternative constructions, and equivalents are also encompassed within the scope of the invention. Embodiments of the present invention are not restricted to operation within certain specific environments, but are free to operate within a plurality of environments. Additionally, although method embodiments of the present invention have been described using a particular series of and steps, it should be apparent to those skilled in the art that the scope of the present invention is not limited to the described series of transactions and steps.

Further, while embodiments of the present invention have been described using a particular combination of hardware, it should be recognized that other combinations of hardware are also within the scope of the present invention. The specification and drawings are, accordingly, to be regarded in an illustrative rather than a restrictive sense. It will, however, be evident that additions, subtractions, deletions, and other modifications and changes may be made thereunto without departing from the broader spirit and scope.

What is claimed is:

1. A bioresorbable bone implant with inside-out resorption for bone and tissue integration, the implant consisting essentially of:
   a porous scaffold structure having a first porosity comprising poly(propylene carbonate), which provides structural integrity at an implant location;
   about 20% to about 40% by weight of starch, wherein the starch has a particle size of 5 μm to 30 μm, which creates additional pores for a second porosity in the scaffold for bone ingrowth and osseointegration in an implant state; and,
   about 20% to about 30% by weight of a bone integrating component which is bioglass 45s5, wherein the starch and the bioglass 45s5 are distributed throughout the poly(propylene carbonate); and
   wherein the bioresorbable bone implant is in a moldable putty state at about 45° C. and a hardened state at about 37° C.

2. The bioresorbable bone implant of claim 1, wherein said starch comprises corn or maze.

3. The bioresorbable bone implant of claim 1, wherein the starch has a particle size of 30 μm.

4. The bioresorbable bone implant of claim 1, wherein the bioglass 45s5 is in the form of particles, fibers, or whiskers.

5. The bioresorbable bone implant of claim 1, wherein the bioglass 45s5 has a particle size of 1 μm to 20 μm.

6. The bioresorbable bone implant of claim 1, wherein the poly(propylene carbonate) is porous.

7. The bioresorbable bone implant of claim 6, wherein the poly(propylene carbonate) has a pore size of 50 μm to 400 μm.

8. The bioresorbable bone implant of claim 6, wherein the poly(propylene carbonate) has a porosity of 10% to 90%.

* * * * *